United States Patent
Stainsby

(10) Patent No.: US 11,333,729 B2
(45) Date of Patent: May 17, 2022

(54) MAGNETIC RESONANCE IMAGING OF DIFFERENT NUCLEAR SPIN SPECIES WITH THE SAME RADIO FREQUENCY COIL

(71) Applicant: Synaptive Medical Inc., Toronto (CA)

(72) Inventor: Jeff A. Stainsby, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 0 days.

(21) Appl. No.: 17/006,249

(22) Filed: Aug. 28, 2020

(65) Prior Publication Data
US 2020/0393528 A1 Dec. 17, 2020

Related U.S. Application Data

(63) Continuation of application No. 15/505,021, filed as application No. PCT/IB2016/053135 on May 27, 2016, now Pat. No. 10,802,094.

(51) Int. Cl.
| | | |
|---|---|---|
| G01R 33/44 | (2006.01) | |
| A61B 5/055 | (2006.01) | |
| G01R 33/36 | (2006.01) | |
| G01R 33/38 | (2006.01) | |
| G01R 33/54 | (2006.01) | |

(52) U.S. Cl.
CPC ............ G01R 33/446 (2013.01); A61B 5/055 (2013.01); G01R 33/3635 (2013.01); G01R 33/38 (2013.01); G01R 33/54 (2013.01)

(58) Field of Classification Search
CPC ..... G01R 33/38; G01R 33/3635; G01R 33/54
See application file for complete search history.

(56) References Cited

U.S. PATENT DOCUMENTS

| | | |
|---|---|---|
| 5,860,921 A | 1/1999 | Ma |
| 5,958,372 A | 9/1999 | Ladd |
| 6,252,405 B1 | 6/2001 | Watkins |
| 6,333,149 B1 | 12/2001 | Sem |
| 7,298,602 B2 | 11/2007 | Knight |
| 7,795,869 B1 | 9/2010 | Bydder |
| 2007/0014448 A1* | 1/2007 | Wheeler ............... G06T 7/0012 382/128 |
| 2008/0246366 A1 | 10/2008 | Burgener |
| 2009/0140738 A1* | 6/2009 | Desvaux ............ G01R 33/3628 324/313 |

(Continued)

FOREIGN PATENT DOCUMENTS

DE 102008020574 10/2009

OTHER PUBLICATIONS

Hilal, S. K., et al. "In vivo NMR imaging of sodium-23 in the human head." Journal of computer assisted tomography9.1 (1985): 1-7.

(Continued)

*Primary Examiner* — Alvaro E Fortich

(57) ABSTRACT

Systems and methods for magnetic resonance imaging ("MRI") of multiple different nuclear spin species using the same radio frequency ("RF") coil are described. Generally, multiple different nuclear spin species are imaged using the same RF coil by using an MRI system whose magnetic field can be rapidly ramped between a number of different, and arbitrary, magnetic field strengths. The magnetic field of this MRI system can be ramped to different values in reasonable amounts of time (e.g., in a time frame that is feasible within an imaging study).

21 Claims, 2 Drawing Sheets

(56) References Cited

U.S. PATENT DOCUMENTS

| | | | |
|---|---|---|---|
| 2011/0115487 A1 | 5/2011 | Grodzki | |
| 2012/0112748 A1 | 5/2012 | Hetherington | |
| 2013/0211236 A1 | 8/2013 | Beck | |
| 2013/0251227 A1 | 9/2013 | Wang | |
| 2013/0285659 A1 | 10/2013 | Sohn | |
| 2014/0055140 A1 | 2/2014 | Umeda et al. | |
| 2016/0091578 A1* | 3/2016 | Schoessow | G01R 33/3614 |
| | | | 324/309 |

OTHER PUBLICATIONS

International Search Report and Written Opinion, dated Sep. 19, 2016, 17 pages.
Massachusetts Institute of Technology NMR Frequency Table. Department of Chemistry Instrumentation Facility. Feb. 27, 2014 Retrieved from the Internet: http://web.mit.edu/speclab/www/Facility/nmrfreq.html>.
Moser E. Ultra-high-field magnetic resonance: Why and when?. World J Radiol. 2010;2(1):37-40.
Nagel AM, et al., Parameter Optimization for 7T 23Na-MRI. Proc Intl Soc Mag Reson Med. 2009;17:2465.
Nagel, A. M., et al. "Skeletal muscle MR imaging beyond protons: with a focus on sodium MRI in musculoskeletal applications." Magnetic Resonance Imaging of the Skeletal Musculature. Springer, Berlin, Heidelberg, 2013. 115-133.
Schad, L. et al., (2008). Hyperpolarized 3He Magnetic Resonance Imaging of the Human Lung . . . [online] Umm.uni-heidelberg.de. Available at: https://www.umm.uni-heidelberg.de/inst/cbtm/ckm/research/radiotherapy/helium/schad/is_96he.html [Accessed Feb. 27, 2019].
Winkler SS. Sodium-23 magnetic resonance brain imaging. Neuroradiology. 1990;32:416-420.

* cited by examiner

MAGNETIC RESONANCE IMAGING OF DIFFERENT NUCLEAR SPIN SPECIES WITH THE SAME RADIO FREQUENCY COIL

CROSS-REFERENCE TO RELATED APPLICATIONS

This application is a continuation of U.S. patent application Ser. No. 15/505,021 filed Feb. 17, 2017, which represents the national stage entry of PCT International Application PCT/IB2016/053135 filed May 27, 2016. The contents of this application are hereby incorporated by reference as if set forth in their entirety herein.

BACKGROUND OF THE INVENTION

Magnetic resonance imaging ("MRI") proceeds by exciting a nuclear spin species with radio frequency ("RF") pulse tuned to the resonance frequency (i.e., the Larmor frequency) of that particular nuclear spin species. After the RF pulse is turned off, the nuclear spin species generates magnetic resonance signals as it relaxes back to equilibrium. These signals are detected by the MRI system and images are reconstructed therefrom.

MRI is capable of imaging signals arising from multiple different nuclear spin species. Conventionally, MRI is used to image hydrogen nuclei (e.g., protons) bound to water molecules in tissue. However, MRI can also be used to image non-proton nuclear spin species, including but not limited to $^3$He, $^{13}$C, $^{19}$F, $^{23}$Na, $^{31}$P, and $^{129}$Xe.

Different nuclear spin species possess fundamentally different gyromagnetic ratios, meaning that they resonate at different frequencies for a given applied magnetic field. For an MRI system to be sensitive to signals at a given frequency requires tuned RF transmit and receive coils and digital sampling rates that are appropriate over narrow bands of frequencies.

To image both proton and non-proton nuclear spin species on a specific MRI system requires either different RF coils and electronics for each different nuclear spin species, or RF coils that are sensitive to multiple different frequency bands. In the first arrangement, the different RF coils and electronics must be switch between imaging sessions. In the second arrangement, coil performance is compromised (e.g., by requiring wide bandwidths, which result in lower sensitivity and poor quality imaging) and require hardware components with increased costs and complexities.

Thus, there is a need for a system and method that provide the ability to image multiple different nuclear spin species with a single MRI system and single RF coil.

SUMMARY OF THE INVENTION

The present invention overcomes the aforementioned drawbacks by providing a method for acquiring magnetic resonance data from different nuclear spin species with a magnetic resonance imaging ("MRI") system. First data are acquired from a first nuclear spin species in a subject using the MRI system and a radio frequency ("RF") coil tuned to a frequency band containing a first Larmor frequency of the first nuclear spin species at a first magnetic field strength. A magnetic field of the MRI system is ramped from the first magnetic field strength to a second magnetic field strength at which a second Larmor frequency of a second nuclear spin species is substantially similar to the first Larmor frequency. Second data are acquired from the second nuclear spin species in the subject using the MRI system and the RF coil tuned to the frequency band containing the first Larmor frequency. Images can be reconstructed from the first and second data, where the images reconstructed from the first data depict the first nuclear spin species and images reconstructed from the second data depict the second nuclear spin species.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here are systems and methods for magnetic resonance imaging ("MRI") of multiple different nuclear spin species using the same radio frequency ("RF") coil. Generally, multiple different nuclear spin species are imaged using the same RF coil by using an MRI system whose magnetic field can be rapidly ramped between a number of different, and arbitrary, magnetic field strengths. The magnetic field of this MRI system can be ramped to different values in reasonable amounts of time (e.g., in a time frame that is feasible within an imaging study). As one example, the MRI system can be ramped to magnetic field strengths in a range of 0-3.0 T on the order of minutes (e.g., 30 minutes or less). An example of such a system is described in co-pending PCT Application Serial No. PCT/IB2015/057979. With this type of system, the main magnetic field can be ramped to different strengths depending on the amount of applied current.

Accordingly, imaging of multiple different nuclear spin species can be carried out using a single magnet system and a single RF coil. As a result, multinuclear imaging can be performed without moving the object between scans, which allows for direct comparisons of the images obtained from the multiple different nuclear spin species (e.g., proton and non-proton images). The systems and methods described here thus eliminate the need for complicated and costly additional system components (e.g., broadband electronics, multiple or multi-tuned RF coils). In addition, by ramping up the magnetic field strength while using the same RF coil, a higher quality image can be obtained of certain non-proton nuclear spin species, which may otherwise be difficult to reliably image.

By ramping the main magnetic field of the MRI system to specific target field strengths, the resonant frequency of different nuclear spin species can be made to fall within a particular band of frequencies in which the transmit and receive RF coil and system electronics are designed. This band of frequencies can be narrow, such as on the order of 1 MHz. By adjusting the main magnetic field of the MRI system, non-proton nuclei can be made to produce signals that are analogous to proton nuclei signals.

Figure 1:
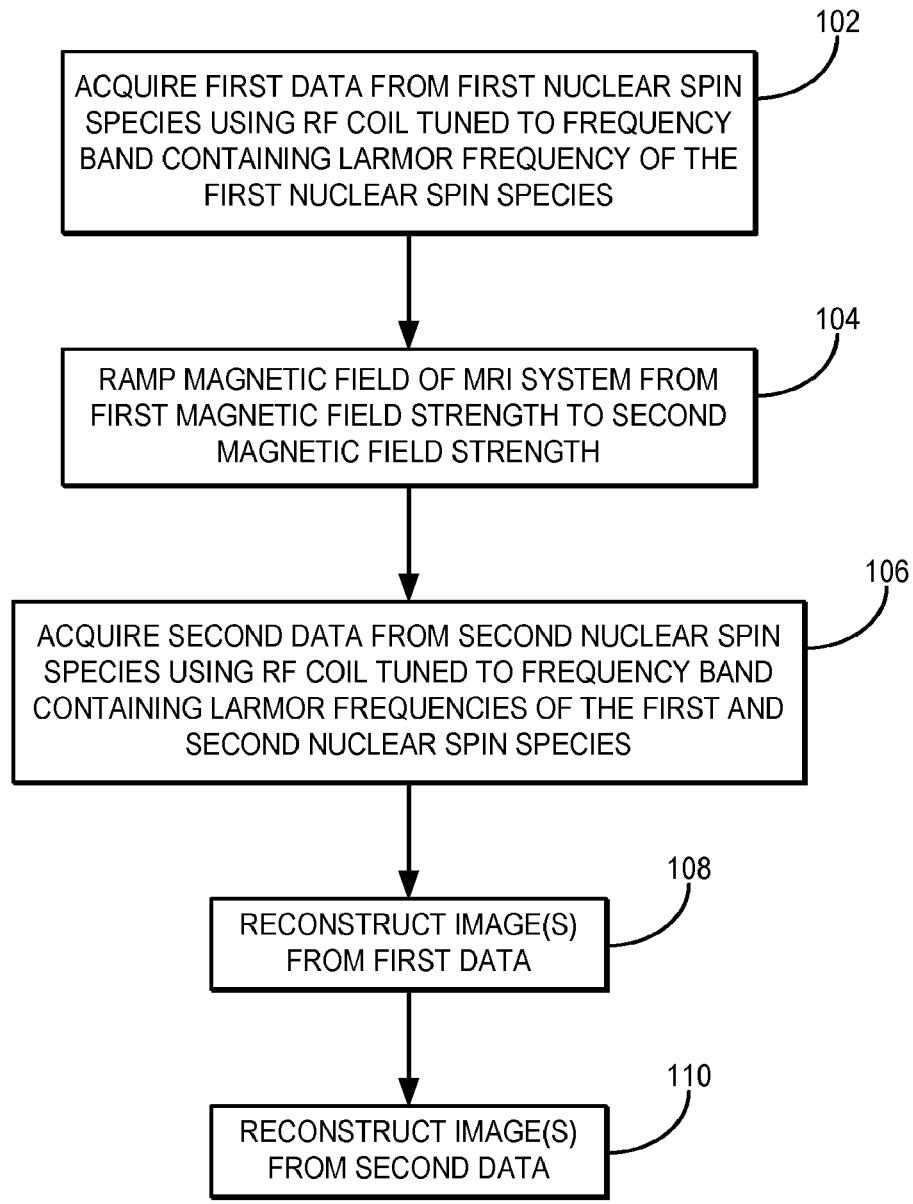
FIG. 1 is a flowchart setting forth the steps of an example method for imaging different nuclear spin species using a single MRI system and a single RF coil.

Referring now to FIG. 1, a flowchart is illustrated as setting forth the steps of an example method for imaging multiple different nuclear spin species using a single MRI system and a single RF coil. The method includes acquiring first data from a first nuclear spin species using the MRI system and the RF coil, as indicated at step 102. For this acquisition, the RF coil is tuned to a frequency band containing the Larmor frequency of the first nuclear spin species at a first magnetic field strength.

The magnetic field of the MRI system is then ramped from the first magnetic field strength to a second magnetic field strength, as indicated at step 104. This second magnetic field strength is selected to be a magnetic field strength at which the Larmor frequency of a second nuclear spin species is substantially similar to the Larmor frequency of the first nuclear spin species at the first magnetic field strength. The second magnetic field strength can be selected such that the Larmor frequency of the second spin species is within the same frequency band as the first Larmor frequency. As one example, the frequency band can be around 1 MHz or less. In other examples, the frequency band can be around 2 MHz or less. It will be appreciated that other, broader, frequency bands can also be used.

Table 1 provides non-limiting examples of Larmor frequencies in a 1 MHz frequency band centered around 22 MHz for various different nuclear spin species, as well as the corresponding magnetic field strengths associated with those Larmor frequencies.

TABLE 1

Example Larmor Frequencies and Magnetic Field Strengths for Various Nuclear Spin Species

| Spin Species | Gyromagnetic Ratio (MHz/T) | Magnetic Field Strength (T) | Larmor Frequency (MHz) |
|---|---|---|---|
| $^1$H | 42.58 | 0.52 | 22.14 |
| $^3$He | 32.43 | 0.68 | 22.05 |
| $^{13}$C | 10.71 | 2.05 | 21.96 |
| $^{19}$F | 40.05 | 0.55 | 22.03 |
| $^{23}$Na | 11.26 | 1.95 | 21.96 |
| $^{31}$P | 17.24 | 1.28 | 22.07 |
| $^{129}$Xe | 11.78 | 1.87 | 22.03 |

After the magnetic field strength of the MRI system is ramped to the second magnetic field strength, second data are acquired from the second nuclear spin species using the MRI system and the RF coil, as indicated at step 106. In some applications, a chemical or contrast agent containing the second nuclear spin species can be administered to the object or subject being imaged. For example, hyperpolarized $^3$He or $^{129}$Xe gas can be administered to a subject, hyperpolarized $^{13}$C can be administered to a subject, or so on. In other applications, the natural abundance of the second nuclear spin species in the object or subject being imaged can be relied upon for imaging.

The RF coil is still tuned to the frequency band containing the first Larmor frequency, and because the second magnetic field strength was selected such that the Larmor frequency of the second nuclear spin species is contained in this same frequency band, the RF coil can be operated to acquire data from the second nuclear spin species without retuning. Thus, the second data can be acquired serially from the object (or subject) from which the first data are acquired without moving the object (or subject).

One or more images can then be reconstructed from the first data, as indicated at step 108. Likewise, one or more images can be reconstructed from the second data, as indicated at step 110. The first images depict the first nuclear spin species, and the second images depict the second nuclear spin species. Because the first data and second data are acquired with the same MRI system and RF coil, the first and second images are inherently co-registered. As such, direct comparisons between the first and second images can be reliably performed. Similarly, the first and second images can be overlaid to form combined or composite images that depict both the first and second nuclear spin species.

As a non-limiting example, the MRI system can be initialized to have a magnetic field strength of 0.5 T. At this magnetic field strength, the Larmor frequency for hydrogen protons is around 21.29 MHz (i.e., $\omega=\gamma B=42.58\times0.5=21.29$ MHz). Data can be acquired from a subject positioned in the MRI system using an RF coil that is tuned to a narrow frequency band that contains this Larmor frequency. For example, the frequency band can be a 1 MHz frequency band. As another example, the frequency band can be a 2 MHz frequency band.

After the data from the hydrogen protons have been acquired, the magnetic field of the MRI system is ramped to a different magnetic field strength that is selected such that the Larmor frequency of a second nuclear spin species to be imaged is within the same frequency band as the first Larmor frequency. For example, if the second nuclear spin species to be imaged is $^3$He, the magnetic field strength of the MRI system can be ramped from 0.5 T to 0.68 T, at which the Larmor frequency of $^3$He nuclei is around 22.05 MHz. Data are then acquired from this second spin species.

By using an RF coil and corresponding electronics that are tuned to a frequency band that contains both the first Larmor frequency (21.29 MHz) and the second Larmor frequency (22.05 MHz), the same RF coil can now be used to acquired data from $^3$He nuclei without having to move the subject to change RF coils and without needing wideband RF electronics with poorer sensitivity. In this example, because the magnetic field strength is increased to image the $^3$He nuclei, better sensitivity will be achieved than using a different RF coil that is tuned to the $^3$He Larmor frequency at 0.5 T.

Images reconstructed from these first and second data can then be overlaid. In the example above, the first images depict tissues in the subject and the second images depict $^3$He nuclei (e.g., $^3$He nuclei administered as a gas to the subject's lungs). Overlaying these images can provide important information between lung structure and physiology. Because the subject does not need to be moved between acquiring the first and second data, the first and second images will inherently depict the same spatial region. Accordingly, no image registration is required because the position of the subject relative to the MRI system (e.g., the position of the subject in the bore of the MRI system) does not need to be changed between the two data acquisitions. If minor subject motion occurred between the first and second data acquisitions, simple registration can be performed, such as by using a fiducial marker.

Figure 2:
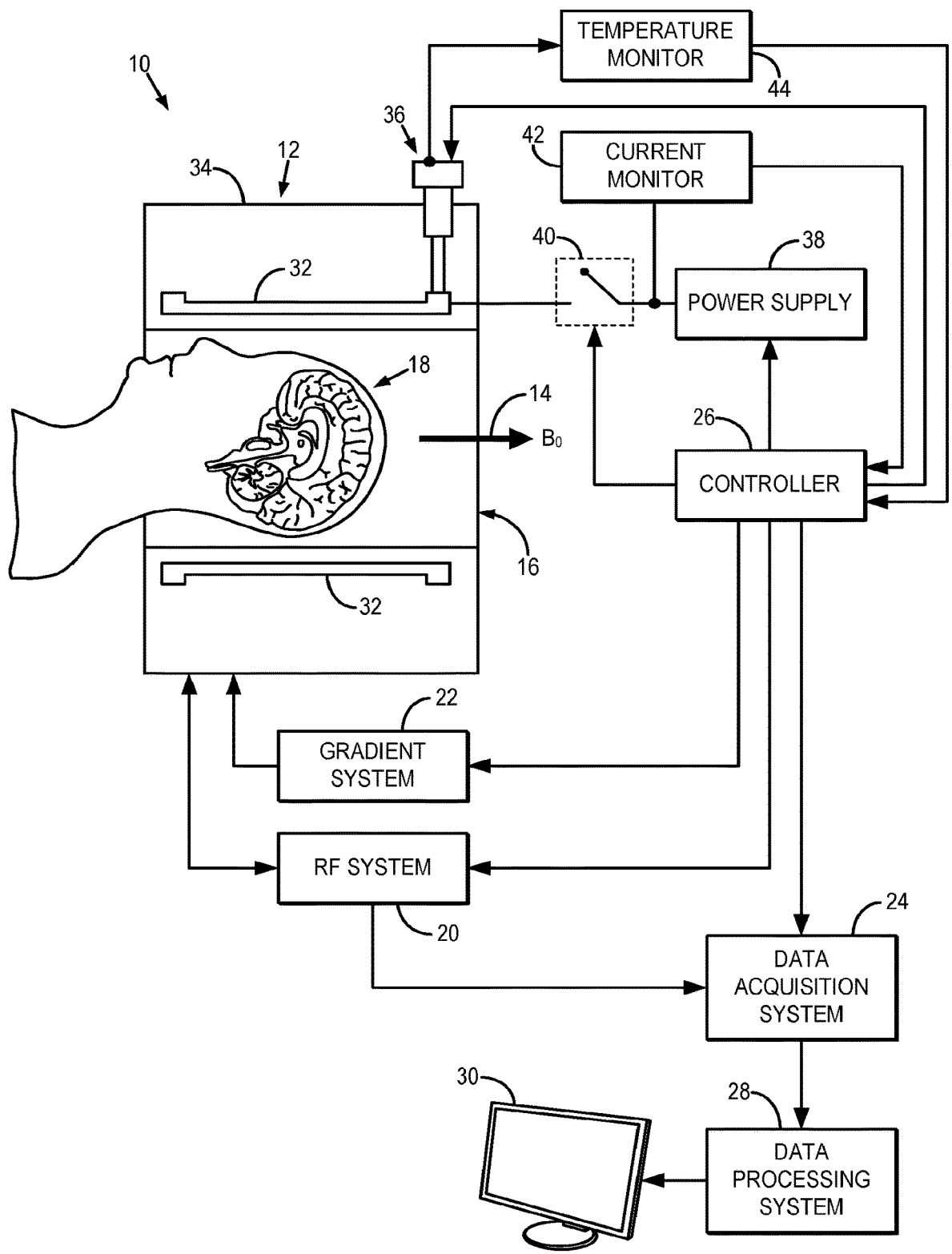
FIG. 2 is a block diagram of an example MRI system that can implement the methods described here.

One example of an MRI system that can implement the methods described here is shown in FIG. 2. The MRI system 10 can be operated to rapidly ramp its magnetic field from a first magnetic field strength to a second magnetic field strength. The MRI system 10 generally includes a magnet assembly 12 for providing a magnetic field 14 that is substantially uniform within a bore 16 that may hold a subject 18 or other object to be imaged. The magnet assembly 12 supports a radio frequency ("RF") coil that may provide an RF excitation to nuclear spins in the subject 18 or object positioned within the bore 16. The RF coil communicates with an RF system 20 producing the necessary electrical waveforms, as is understood in the art.

The magnet assembly 12 also supports three axes of gradient coils (not shown) of a type known in the art, and which communicate with a corresponding gradient system 22 providing electrical power to the gradient coils to produce magnetic field gradients, $G_x$, $G_y$, and $G_z$ over time. A data acquisition system 24 connects to RF reception coils (not shown) that are supported within the magnet assembly 12 or positioned within bore 16.

The RF system 20, gradient system 22, and data acquisition system 24 each communicates with a controller 26 that generates pulse sequences that include RF pulses from the RF system 20 and gradient pulses from gradient system 22. The data acquisition system 24 receives magnetic resonance signals from the RF system 20 and provides the magnetic resonance signals to a data processing system 28, which operates to process the magnetic resonance signals and to reconstruct images therefrom. The reconstructed images can be provided to a display 30 for display to a user.

The magnet assembly 12 includes one or more magnet coils 32 housed in a vacuum housing 34, which generally provides a cryostat for the magnet coils 32. The magnet coils are mechanically cooled by a mechanical cryocooler 36, such as a Gifford-McMahon ("GM") cryocooler or a pulse tube cryocooler. In one example configuration, the cryocooler can be a Model RDK-305 Gifford-McMahon cryocooler manufactured by Sumitomo Heavy Industries (Japan). In general, the cryocooler 36 is in thermal contact with the magnet coils 32 and is operable to lower the temperature of the magnet coils 32 and to maintain the magnet coils 32 and a desired operating temperature.

The magnet coils 32 are composed of a superconducting material and therefore provide a superconducting magnet. The superconducting material is preferably selected to be a material with a suitable critical temperature such that the magnet coils 32 are capable of achieving desired magnetic field strengths over a range of suitable temperatures. As one example, the superconducting material can be niobium ("Nb"), which has a transition temperature of about 9.2 K. As another example, the superconducting material can be niobium-titanium ("NbTi"), which has a transition temperature of about 10 K. As still another example, the superconducting material can be triniobium-tin ("$Nb_3Sn$"), which has a transition temperature of about 18.3 K.

The choice of superconducting material will define the range of magnetic field strengths achievable with the magnet assembly 12. Preferably, the superconducting material is chosen such that magnetic field strengths in the range of about 0.0 T to about 3.0 T can be achieved over a range of temperatures that can be suitably achieved by the cryocooler 36. In some configurations, however, the superconducting material can be chosen to provide magnetic field strengths higher than 3.0 T.

The cryocooler 36 is operable to maintain the magnet coils 32 at an operational temperature at which the magnet coils 32 are superconducting, such as a temperature that is below the transition, or critical, temperature for the material of which the magnet coils 32 are composed. As one example, a lower operational temperature limit can be about 4 K and an upper operational temperature limit can be at or near the transition, or critical, temperature of the superconducting material of which the magnet coils 32 are composed.

The current density in the magnet coils 32 in the MRI system 10 is controllable to rapidly ramp up or ramp down the magnetic field 14 generated by the magnet assembly 12 while controlling the temperature of the magnet coils 32 with the cryocooler 36 to keep the temperature below the transition temperature of the superconducting material of which the magnet coils 32 are composed. As one example, the magnetic field 14 can be ramped up or ramped down on the order of minutes, such as fifteen minutes or less.

In general, the current density in the magnet coils 32 can be increased or decreased by connecting the magnet coils 32 to a circuit with a power supply 38 that is in electrical communication with the magnet coils 32 via a switch 40 and operating the power supply 38 to increase or decrease the current in the connected circuit. The switch 40 is generally a superconducting switch that is operable between a first, closed, state and a second, open, state.

When the switch 40 is in its open state, the magnet coils 32 are in a closed circuit, which is sometimes referred to as a "persistent mode." In this configuration, the magnet coils 32 are in a superconducting state so long as the temperature of the magnet coils 32 is maintained at a temperature at or below the transition temperature of the superconducting material of which they are composed.

When the switch 40 is in the closed state, however, the magnet coils 32 and the power supply 38 can be placed in a connected circuit, and the current supplied by the power supply 38 and the current in the magnet coils 32 will try to equalize. For instance, if the power supply 38 is operated to supply more current to the connected circuit, the current in the magnet coils 32 will increase, which will increase the strength of the magnetic field 14. On the other hand, if the power supply 38 is operated to decrease the current in the connected circuit, the current in the magnet coils 32 will decrease, which will decrease the strength of the magnetic field 14.

It will be appreciated by those skilled in the art that any suitable superconducting switch can be used for selectively connecting the magnet coils 32 and power supply 38 into a connected circuit; however, as one non-limiting example, the switch 40 may include a length of superconducting wire that is connected in parallel to the magnet coils 32 and the power supply 38. To operate such a switch 40 into its closed state, a heater in thermal contact with the switch 40 is operated to raise the temperature of the superconducting wire above its transition temperature, which in turn makes the wire highly resistive compared to the inductive impedance of the magnet coils 32. As a result, very little current will flow through the switch 40. The power supply 38 can then be placed into a connected circuit with the magnet coils 32.

When in this connected circuit, the current in the power supply 38 and the magnet coils 32 will try to equalize; thus, by adjusting the current supplied by the power supply 38, the current density in the magnet coils 32 can be increased or decreased to respectively ramp up or ramp down the magnetic field 14. To operate the switch 40 into its open state, the superconducting wire in the switch 40 is cooled below its transition temperature, which places the magnet coils 32 back into a closed circuit, thereby disconnecting the power supply 38 and allowing all of the current to flow through the magnet coils 32.

When the magnet coils 32 are in the connected circuit with the power supply 38, the temperature of the magnet coils 32 will increase as the current in the connected circuit equalizes. Thus, the temperature of the magnet coils 32 should be monitored to ensure that the temperature of the magnet coils 32 remains below the transition temperature for the superconducting material of which they are composed. Because placing the magnet coils 32 into a connected circuit with the power supply 38 will tend to increase the temperature of the magnet coils 32, the rate at which the magnetic field 14 can be ramped up or ramped down will depend in part on the cooling capacity of the cryocooler 36. For instance, a cryocooler with a larger cooling capacity will be able to more rapidly remove heat from the magnet coils 32 while they are in a connected circuit with the power supply 38.

The power supply 38 and the switch 40 operate under control from the controller 26 to provide current to the magnet coils 32 when the power supply 38 is in a connected circuit with the magnet coils 32. A current monitor 42 measures the current flowing to the magnet coils 32 from the power supply 38, and a measure of the current can be provided to the controller 26 to control the ramping up or ramping down of the magnetic field 14. In some configurations, the current monitor 42 is integrated into the power supply 38.

A temperature monitor 44 is in thermal contact with the magnet assembly 12 and operates to measure a temperature of the magnet coils 32 in real-time. As one example, the temperature monitor 44 can include a thermocouple temperature sensor, a diode temperature sensor (e.g., a silicon diode or a GaAlAs diode), a resistance temperature detector ("RTD"), a capacitive temperature sensor, and so on. RTD-based temperature sensors can be composed of ceramic oxynitride, germanium, or ruthenium oxide. The temperature of the magnet coils 32 is monitored and can be provided to the controller 26 to control the ramping up or ramping down of the magnetic field 14.

In operation, the controller 26 is programmed to ramp up or ramp down the magnetic field 14 of the magnet assembly 12 in response to instructions from a user. As mentioned above, the magnetic field 14 can be ramped down by decreasing the current density in the magnet coils 32 by supplying current to the magnet coils 32 from the power supply 38 via the switch 40, which is controlled by the controller 26. Likewise, the strength of the magnetic field 14 can be ramped up by increasing the current density in the magnet coils 32 by supplying current to the magnet coils 32 from the power supply 38 via the switch 40, which is controlled by the controller 26.

The controller 26 is also programmed to monitor various operational parameter values associated with the MRI system 10 before, during, and after ramping the magnetic field 14 up or down. As one example, as mentioned above, the controller 26 can monitor the current supplied to the magnet coils 32 by the power supply 38 via data received from the current monitor 42. As another example, as mentioned above, the controller 26 can monitor the temperature of the magnet coils 32 via data received from the temperature monitor 44. As still another example, the controller 26 can monitor the strength of the magnetic field 14, such as by receiving data from a magnetic field sensor, such as a Hall probe or the like, positioned in or proximate to the bore 16 of the magnet assembly 12.

One or more computer systems can be provided with the MRI system 10 for processing acquired data in accordance with the methods described above. As one example, the data processing system 28 can be used to process the acquired data.

For example, the data processing system 28 can receive magnetic resonance data from the data acquisition system 24 and processes it in accordance with instructions downloaded from an operator workstation. Such processing may include those methods described above for reconstructing images and producing composite images by overlaying image depicting one nuclear spin species with images depicting a different nuclear spin species.

Images reconstructed by the data processing system 28 can be conveyed back to the operator workstation for storage, and real-time images can be stored in a memory, from which they may be output to display 30.

The MRI system 10 may also include one or more networked workstations. By way of example, a networked workstation may include a display; one or more input devices, such as a keyboard and mouse; and a processor. The networked workstation may be located within the same facility as the MRI system 10, or in a different facility, such as a different healthcare institution or clinic.

The networked workstation, whether within the same facility or in a different facility as the MRI system 10, may gain remote access to the data processing system 28 via a communication system. Accordingly, multiple networked workstations may have access to the data processing system 28. In this manner, magnetic resonance data, reconstructed images, or other data may be exchanged between the data processing system 28 and the networked workstations, such that the data or images may be remotely processed by a networked workstation. This data may be exchanged in any suitable format, such as in accordance with the transmission control protocol ("TCP"), the internet protocol ("IP"), or other known or suitable protocols.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for acquiring magnetic resonance data from different nuclear spin species with a magnetic resonance imaging (MRI) system, the steps of the method comprising:
   acquiring first data from a first nuclear spin species in a subject and second data from a second nuclear spin species in the subject using the MRI system and a radio frequency (RF) coil tuned to a frequency band by:
   (a) acquiring the first data from the first nuclear spin species using the RF coil tuned to the frequency band when a main magnetic field, $B_0$, of the MRI system is at a first magnetic field strength at which a Larmor frequency corresponding to the first nuclear spin species is within the frequency band of the RF coil and the Larmor frequency corresponding to the second nuclear spin species is outside the frequency band of the RF coil;
   (b) ramping the main magnetic field, $B_0$, of the MRI system from the first magnetic field strength to a second magnetic field strength in order to shift the Larmor frequency corresponding to the second nuclear spin species into the frequency band of the RF coil; and
   (c) acquiring the second data from the second nuclear spin species in the subject using the RF coil tuned to the frequency band when the main magnetic field, $B_0$, of the MRI system is at the second magnetic field strength.

2. The method as recited in claim 1, further comprising reconstructing a first image from the first data and reconstructing a second image from the second data, wherein the first image depicts the first nuclear spin species and the second image depicts the second nuclear spin species.

3. The method as recited in claim 1, wherein the RF coil is a multichannel RF coil.

4. The method as recited in claim 1, wherein the first nuclear spin species includes $^1$H.

5. The method as recited in claim 4, wherein the second nuclear spin species includes one of $^3$He, $^{13}$C, $^{19}$F, $^{23}$Na, $^{31}$P, or $^{129}$Xe.

6. The method as recited in claim 1, wherein the first nuclear spin species is selected from the group consisting of $^1$H, $^3$He, $^{13}$C, $^{19}$F, $^{23}$Na, $^{31}$P, and $^{129}$Xe, and the second nuclear spin species is selected from the group consisting of $^1$H, $^3$He, $^{13}$C, $^{19}$F, $^{23}$Na, $^{31}$P, and $^{129}$Xe.

7. The method as recited in claim 1, wherein the first magnetic field strength is 0.5 Tesla, and the frequency band of the RF coil spans a frequency range of 21 MHz to 23 MHz.

8. The method as recited in claim 7, wherein the frequency band of the RF coil spans a frequency range of 21.5 Mhz to 22.5 MHz.

9. The method as recited in claim 1, wherein the frequency band of the RF coil is at most 2 MHz.

10. The method as recited in claim 9, wherein the frequency band of the RF coil is at most 1 MHz.

11. The method as recited in claim 1, wherein the main magnetic field, $B_0$, of the MRI system is ramped from the first magnetic field strength to the second magnetic field strength in less than 30 minutes.

12. The method as recited in claim 1, wherein a position of the subject relative to the MRI system is not changed between acquiring the first data and acquiring the second data.

13. A method for acquiring magnetic resonance data from different nuclear spin species with a magnetic resonance imaging (MRI) system, the steps of the method comprising:
(a) acquiring first data from a first nuclear spin species in a subject and second data from a second nuclear spin species in the subject using the MRI system and a radio frequency (RF) coil tuned to a frequency band by:
  (i) acquiring the first data from the first nuclear spin species using the RF coil tuned to the frequency band when a main magnetic field, $B_0$, of the MRI system is at a first magnetic field strength at which a Larmor frequency corresponding to the first nuclear spin species is within the frequency band of the RF coil and the Larmor frequency corresponding to the second nuclear spin species is outside the frequency band of the RF coil;
  (ii) ramping the main magnetic field, $B_0$, of the MRI system from the first magnetic field strength to a second magnetic field strength in order to shift the Larmor frequency corresponding to the second nuclear spin species into the frequency band of the RF coil;
  (iii) acquiring the second data from the second nuclear spin species in the subject using the RF coil tuned to the frequency band when the main magnetic field, $B_0$, of the MRI system is at the second magnetic field strength
(b) reconstructing a first image from the first data and reconstructing a second image from the second data, wherein the first image depicts the first nuclear spin species and the second image depicts the second nuclear spin species; and
(c) generating a combined image by selectively combining the first image and the second image.

14. The method as recited in claim 13, wherein the first nuclear spin species includes $^1$H.

15. The method as recited in claim 14, wherein the second nuclear spin species includes one of $^3$He, $^{13}$C, $^{19}$F, $^{23}$Na, $^{31}$P, and $^{129}$Xe.

16. The method as recited in claim 13, wherein the first nuclear spin species is selected from the group consisting of $^1$H, $^3$He, $^{13}$C, $^{19}$F, $^{23}$Na, $^{31}$P, and $^{129}$Xe, and the second nuclear spin species is selected from the group consisting of $^1$H, $^3$He, $^{13}$C, $^{19}$F, $^{23}$Na, $^{31}$P, and $^{129}$Xe.

17. The method as recited in claim 13, wherein the first magnetic field strength is 0.5 Tesla, and the frequency band of the RF coil spans a frequency range of 21 MHz to 23 MHz.

18. The method as recited in claim 17, wherein the frequency band of the RF coil spans a frequency range of 21.5 Mhz to 22.5 MHz.

19. The method as recited in claim 13, wherein the frequency band of the RF coil is at most 2 MHz.

20. The method as recited in claim 19, wherein the frequency band of the RF coil is at most 1 MHz.

21. The method as recited in claim 13, wherein the main magnetic field, $B_0$, of the MRI system is ramped from the first magnetic field strength to the second magnetic field strength in less than 30 minutes.

\* \* \* \* \*